United States Patent
Hansen

(10) Patent No.: US 6,871,093 B2
(45) Date of Patent: Mar. 22, 2005

(54) REPORTING THE STATUS FOR AN EXTERNAL DEFIBRILLATOR WITH AN AUDIBLE REPORT IN RESPONSE TO A SPECIFIED USER INPUT

(75) Inventor: Kim J. Hansen, Renton, WA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 443 days.

(21) Appl. No.: 09/749,620

(22) Filed: Dec. 28, 2000

(65) Prior Publication Data

US 2002/0087195 A1 Jul. 4, 2002

(51) Int. Cl.[7] ................................................. A61N 1/00
(52) U.S. Cl. ............................................. 607/5; 607/29
(58) Field of Search ............................ 607/5, 10, 4, 27, 607/29

(56) References Cited

U.S. PATENT DOCUMENTS

| 5,593,427 | A | | 1/1997 | Gliner et al. | |
|---|---|---|---|---|---|
| 5,607,454 | A | | 3/1997 | Cameron et al. | |
| 5,735,879 | A | | 4/1998 | Gliner et al. | |
| 5,836,993 | A | | 11/1998 | Cole | |
| 5,879,374 | A | | 3/1999 | Powers et al. | |
| 6,006,132 | A | * | 12/1999 | Tacker et al. | 607/5 |
| 6,148,233 | A | * | 11/2000 | Owen et al. | 607/5 |
| 6,366,809 | B1 | * | 4/2002 | Olson et al. | 607/29 |
| 6,438,417 | B1 | * | 8/2002 | Rockwell et al. | 607/27 |

* cited by examiner

*Primary Examiner*—J. Casimer Jacyna
(74) *Attorney, Agent, or Firm*—Tony Piotrowski

(57) ABSTRACT

A defibrillator system including a defibrillator and at least one indicator including at least one visual indicator and/or at least one audible indicator connected to the defibrillator for generating an indication of a functional status of the defibrillator periodically and/or on command by a user.

8 Claims, 3 Drawing Sheets

REPORTING THE STATUS FOR AN EXTERNAL DEFIBRILLATOR WITH AN AUDIBLE REPORT IN RESPONSE TO A SPECIFIED USER INPUT

BACKGROUND OF THE INVENTION

1. Field of the Invention

The present invention relates to a defibrillator system that reports the operational status of a defibrillator included in the system.

2. Description of the Prior Art

Electrotherapy devices are used to provide electric shocks to treat patients for a variety of heart arrhythmias. For example, external defibrillators typically provide relatively high-energy shocks to a patient (as compared to implantable defibrillators), usually through electrodes attached to the patient's torso. External defibrillators are used to convert ventricular fibrillation ("VF") or shockable ventricular tachycardia ("VT") to a normal sinus rhythm. Similarly, external cardioverters can be used to provide paced shocks to convert atrial fibrillation ("AF") to a more normal heart rhythm.

Sudden cardiac arrest ("SCA") is the leading cause of death in the United States. On average, 1000 people per day die; this translates into one death every two minutes. It is likely that these statistics would, at a minimum, hold true for third world countries. However, in view of difficulty in acquiring reliable data, statistics are not widely available.

Most sudden cardiac death is caused by VF, in which the heart's muscle fibers contract without coordination, thereby interrupting normal blood flow to the body. The only effective treatment for VF is electrical defibrillation, which applies an electrical shock to the patient's heart. The electrical shock clears the heart of the abnormal electrical activity (in a process called "defibrillation") by depolarizing a critical mass of myocardial cells to allow spontaneous organized myocardial depolarization to resume.

To be effective, the defibrillation shock must be delivered to the patient within minutes of the onset of VF. Studies have shown that defibrillation shocks delivered within one minute after the onset of VF achieve up to a 100% survival rate. However, the survival rate falls to approximately 30% after only 6 minutes. Beyond 12 minutes, the survival rate approaches zero. Importantly, the more time that passes, the longer the brain is deprived of oxygen and the more likely that brain damage will result. As improved access to defibrillators increases, survival rates from SCA also increase.

Defibrillators must function when their use is required; no time or very little time exists for rehabilitating a non-functional defibrillator in an emergency situation. A defibrillator treats a condition that requires immediate treatment or death could result. If a defibrillator is not functional, within minutes a patient will almost certainly suffer severe permanent damage or die. Additionally, the nature of a defibrillator in that it includes electrical circuitry and a power supply contribute to the requirement that a defibrillator be functional. Unlike a mechanical device, which might be fixable in a short period of time, such is not typically possible for a defibrillator.

A recent trend has placed defibrillators in public places for use in emergency situations prior to arrival of emergency response personnel and in situations, such as on airborne aircraft where emergency response personnel are not available. Concerns regarding the associated with the functionality of a defibrillator rise in connection with such publicly placed defibrillators. Unlike a hospital or ambulance setting where a backup may be available, such a backup may not be available for publicly placed defibrillators.

SUMMARY OF THE INVENTION

The present invention concerns a defibrillator system that includes a defibrillator and at least one indicator. The indicator includes at least one visual indicator and/or at least one audible indicator connected to the defibrillator for periodically and/or as requested by a user generating a visual indication of a functional status of the defibrillator.

Still other objects and advantages of the present invention will become readily apparent by those skilled in the art from a review of the following detailed description. The detailed description shows and describes preferred embodiments of the invention, simply by way of illustration of the best mode contemplated of carrying out the present invention. As will be realized, the invention is capable of other and different embodiments and its several details are capable of modifications in various obvious respects, without departing from the invention. Accordingly, the drawings and description are illustrative in nature and not restrictive.

BRIEF DESCRIPTION OF THE DRAWINGS

Objects and advantages of the present invention will be more clearly understood when considered in conjunction with the accompanying drawings, in which.

DESCRIPTION OF THE PREFERRED EMBODIMENTS

Figure 1:
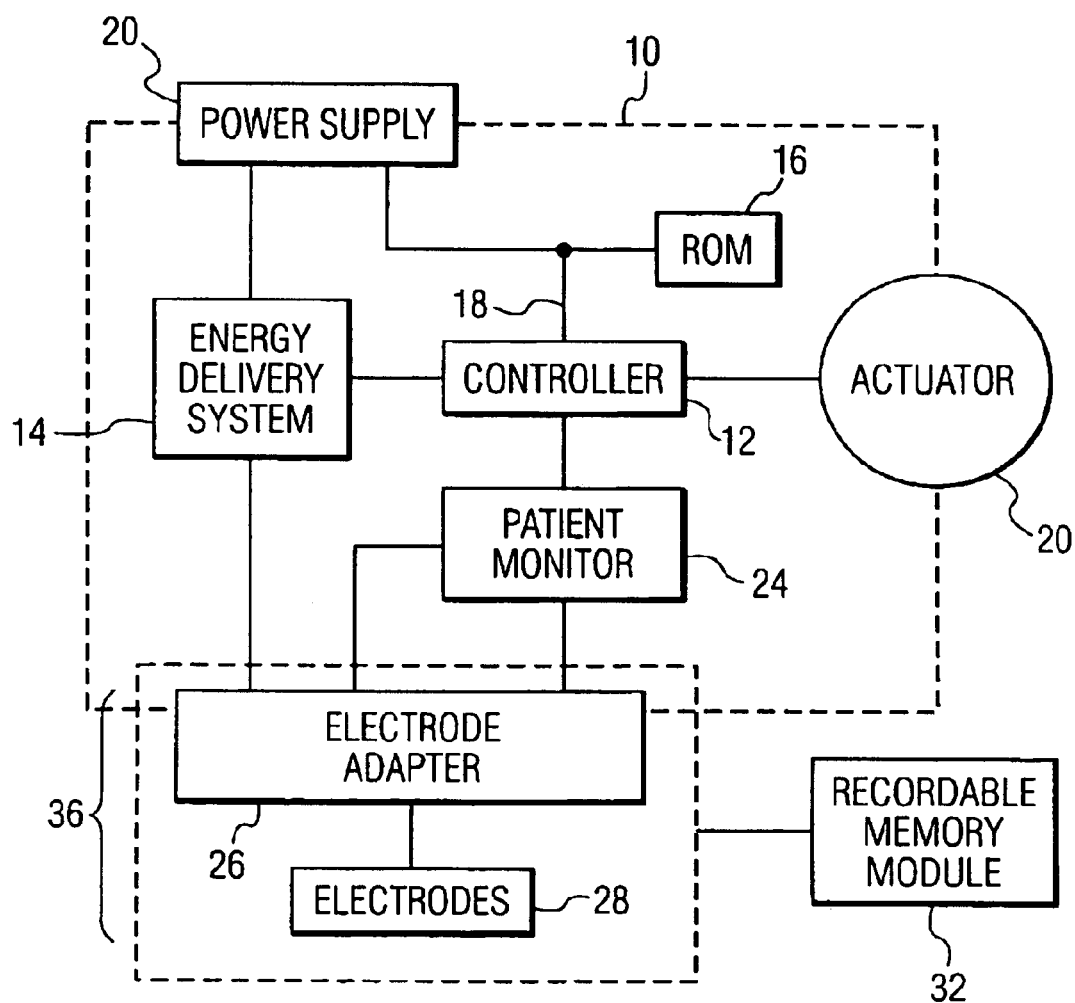
FIG. 1 represents a block diagram illustrating an electrotherapy device showing a detachable electrode system.

FIG. 1 is a block diagram showing a device 10. Device 10 is an electrotherapy device. The device 10 may include the ability to defibrillate, cardiovert, or pace a patient, or a combination of these features. Device 10 has a controller 12 that operates an energy delivery system 14 and performs other aspects of the operation of the device. Software instructions for the operation of the device are accessible from read only memory (ROM), such as incorporated ROM 16. The controller accesses instructions for operation from ROM 16. It should be understood that, in this and other embodiments described below, "controller" means a microprocessor, controller, gate array, other control logic, or any combination of these elements.

Controller 12 communicates with ROM 16 via a memory bus 18. A recordable memory module 32 is attached to device 10 via an electrode system is 36, as shown in FIG. 1. Electrode system 36 includes electrodes 28 and an electrode adapter 26.

Electrode adapter 26 is connected to electrodes 28 and is removably connected to the device 10. A suitable electrode system 36 adaptable for use in this invention would be, for example, Heartstream ForeRunner® electrodes.

Electrodes 28 communicate with a patient monitor 24 via electrode adapter 26 to provide patient ECG data from the patient to the patient monitor 24. Electrodes include electrodes capable of delivering defibrillation, monitoring a patient condition, delivering pacing pulses, or a combination of those features. In an AED, the patient monitor 24 monitors the patient for a heart rhythm and subsequently determines whether the monitored rhythm is shockable. When the rhythm is shockable, the patient monitor 24 then communicates a shock decision to the controller 12. The controller 12, then communicates to the energy delivery system 14. The energy delivery system 14 then delivers a therapeutic energy pulse to the patient (not shown) through electrodes 28 attached to the defibrillator 10 via electrode adapter 26, using the power supply 20 as the energy source.

The power supply may include elements such as batteries, a DC and/or an AC power source. The DC power source could be batteries. The power supply could also include a DC-DC and/or AC to DC converters. Additionally, the power supply could include a high voltage charge circuit. Furthermore, the power supply could include an energy storage capacitor.

Figure 2:
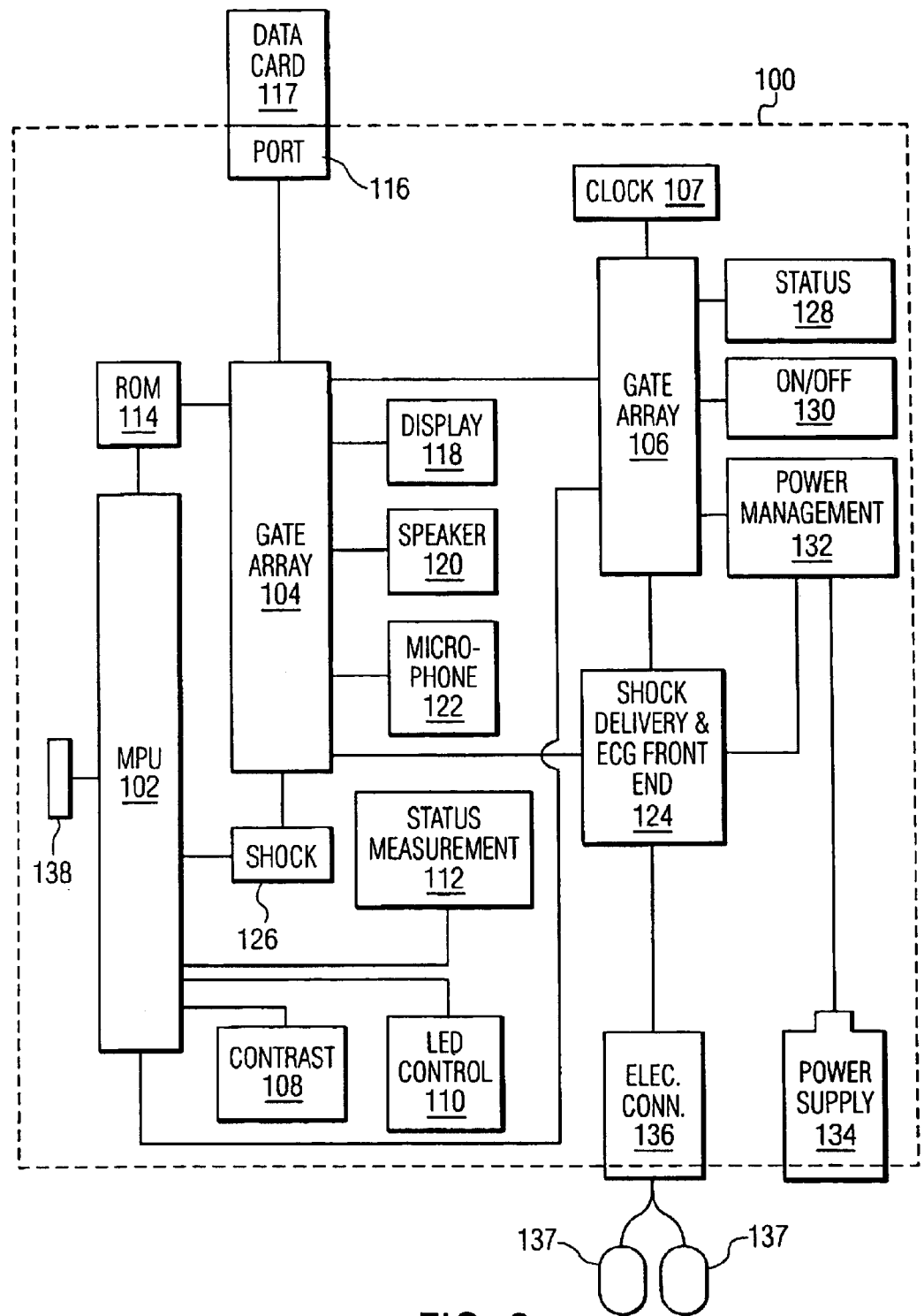
FIG. 2 represents a block diagram illustrating major components of a semi-automatic external defibrillator shown in FIG. 1.

The major components of an AED are shown in FIG. 2 in block diagram form. Further detailed information about the operation of an AED can be obtained in U.S. Pat. No. 5,836,993, to Cole, for "Electrotherapy Device Control System and Method", and U.S. Pat. No. 5,593,427 to Gliner et al., for "Electrotherapy Method," the specifications of both of which are incorporated herein by reference. As will be appreciated by those of skill in the art, the invention can be used in a variety of AEDs and is not limited to this configuration, which is used for illustration purposes only.

In this illustration, defibrillator control functions are divided among a microprocessor unit (MPU) 102 and two custom gate arrays 104 and 106.

MPU 102 performs program steps according to software instructions provided to it from ROM 114. MPU 102 controls the operation of certain buttons (such as display contrast buttons 108) and certain system LED's 110 (such as LED's associated with the shock button and the electrode connector). MPU 102 also receives system status information as shown by block 112.

Gate array 104 implements the memory map to system ROM 114. System ROM 114 is preferably flash ROM, although EPROM or any other electrically erasable and programmable nonvolatile memory could be used. Gate array 104 also controls a display 118, a speaker 120, and a microphone 122. Gate array 104 can actuate a relay within the shock delivery and ECG front-end system 124 in response to actuation of a shock button 126 by a user during treatment mode.

Gate array 106 provides a system monitor function by performing automatic self-tests of the defibrillator and its components. The gate array 106 displays the operational status of the defibrillator on a status display 128. Details of suitable self-tests may be found in U.S. Pat. No. 5,879,374, to Powers et al., for "External Defibrillator with Automated Self-Testing Prior to Use," the specification of which is incorporated herein by reference. Gate array 106 is also the defibrillator's interface with a user-activated on/off switch 130. Gate array 106 controls the power management subsystem 132 to provide power to operate system components from power supply 134 and to provide energy to the shock delivery system's capacitor(s) for a therapeutic shock during treatment mode. Gate array 106 also interfaces with the defibrillator's ECG front end, enables the shock delivery system to deliver a shock in response to detection of a patient ECG pattern requiring treatment (and actuation of the shock button), and controls delivery of the shock to electrode connector 136 in response to shock delivery status information obtained during delivery of the shock. Further information regarding this last function may be found in U.S. Pat. No. 5,735,879 to Gliner et al., for "Electrotherapy Method for External Defibrillators"; and U.S. Pat. No. 5,607,454, to Cameron et al. for "Electrotherapy Method and Apparatus", the specifications of both of which are incorporated herein by reference.

The MPU can send and receive data and operational commands via the wireless communication port 138. This is used to assist manufacturing and to communicate status and use data to external devices. In addition, the port 138 permits remote operation of certain device features such as requesting and receiving device status.

These defibrillator components communicate with each other over suitable communication buses, as shown.

External defibrillator 100 can be operated in different modes, such as self-test mode, stand-by mode, set-up mode, patient treatment mode, training mode and code-transfer mode. The operational characteristics of defibrillator 100 differ in each mode. In addition, the operational characteristics of the defibrillator in any one of the modes can be changed as explained below.

Operation of the external defibrillator of this embodiment commences with the insertion of a power supply 134 or user activation of the power on button. Once gate array 106 confirms that a power supply 134 is inserted, gate array 104 prompts MPU 102 to begin its boot sequence. The boot sequence begins with MPU 102 sending out a series of addresses to ROM 114.

As is known in the art, while in patient treatment mode, the defibrillator 100 typically (1) determines whether electrodes 137 are attached to electrode connector 136; (2) receives ECG information from a patient through such electrodes; (3) analyzes the ECG information to determine whether a therapeutic shock is advised; and (4) delivers a shock to the patient through the electrodes 137 if a shock is advised and if the shock button 126 is actuated by a user.

Most defibrillators include a visual display of some type for indicating whether or not a defibrillator is usable. The displays can commonly include LCD displays, magnetic flip indicators, or LED displays, among others. Typically, the displays always display the status of a defibrillator. When it is desired to ascertain the status of a defibrillator, a user simply views the display.

To extend battery life and reduce the frequency of battery maintenance, displays are designed for minimal power consumption. However, the displays can be expensive and/or still consume too much power. Some devices even require activation of a defibrillator prior to ascertaining and displaying defibrillator status.

The present invention can provide an inexpensive alternative to the currently utilized defibrillator status display devices. Additionally, the present invention can provide a defibrillator display device with a low power consumption. This can reduce consumption of power for the defibrillator or for a power supply for the indicator.

Other advantages of embodiments of the present invention can include providing audio confirmation of the visual indicator. Additionally, the present invention can provide on-demand status for devices with a periodic status indicator. Furthermore, the present invention can provide on-demand status for devices with no visual or audio indicator.

The present invention provides a defibrillator system. The system includes a defibrillator. The defibrillator is connected to a power source. The power source may be a public power grid. Alternatively, a battery may supply the power for the defibrillator. Any suitable power source may be utilized. Batteries or power sources other than the public power grid are typically utilized with defibrillators placed in public locations. This is at least in part to eliminate the need to connect the defibrillators to the public power supply grid and to eliminate the need to move a victim to the location of the defibrillator.

At least one indicator is connected to the defibrillator and may also be connected to the power supply. The indicator indicates the functional or operational status of the defibrillator. Depending upon the embodiment, the indicator may automatically indicate the operational status of the defibrillator and/or automatically indicate the operational status of the defibrillator in response to an inquiry from a user. If the indicator automatically indicates the operational status, the indicator may periodically or constantly indicate the status.

The meaning of status indication produced by the indicator can also change, depending upon the embodiment. For example, the status can include the power level of the battery. The status could also or alternatively include electrode pad functionality. Along these lines, moisture in the electrodes can evaporate making the electrodes non-functional. The functional status of the defibrillator could alternatively include functional status of defibrillator circuitry. The circuitry status could be multi-level. Along these lines, the compromising of functionality as a result of a number of causes could trigger a non-functional indication. Causes could include, for example, lack of a data card or a broken device.

Regardless of the frequency of the indication of the status of the defibrillator, the indicator may have different forms. For example, the indicator may include one or more visual elements and/or one or more audible elements. As is discussed below in greater detail, a variety of visual and audible elements may be suitable for use with the present invention.

One example of a visual indicator element can include one or more light emitting diodes (LEDs). With an automatically indicating embodiment, the LEDs can periodically or constantly produce light to indicate operational status of the defibrillator system. According to one embodiment, the indicator includes an LED that periodically produces light to indicate the operational status of a defibrillator system. The color of the LED could change, based upon whether the defibrillator system is operational. For example, a green LED could indicate an operational defibrillator system and a red LED could indicate a non-functional defibrillator system. One LED may also produce more than one color.

Rather than change color or a different LED producing light to indicate various operational states of a defibrillator system, one or more parameters related to activation of the LED could change based upon the operational status of the defibrillator system. For example, the frequency with which the LED produces light could change with changes in the operational state of the defibrillator system. Along these lines, the frequency could increase or decrease.

A visual indicator could also or alternatively include one or more lights, one or more display elements and/or any other visual indicating elements.

The indicator could also or alternatively include at least one audible indicator. For example, the indicator could include at least one tone-generating element similar to such elements that produce audible beeps on personal computers. One or more speakers could also or alternatively be included to generate more complex audible signals. The speakers, tone-generating elements, or other devices could be those already incorporated into defibrillators. Any audible indicator could also produce speech to indicate status. Any visual indicators included in the present invention could be those already included in defibrillators. The visual indicators could produce words or an indication of status in any other manner.

The audible indicator(s) could periodically produce indications of defibrillator status. Additionally or alternatively, the audible indicators could produce a signal in response to a change in operational status. Furthermore, the audible indicator(s) could produce an indication of defibrillator status in response to a user inquiry.

To indicate changes in defibrillator functional status, alterations could be made to the output produced by an audible indicator. For example, the frequency, volume, pitch, or other parameter characterizing the audible signals produced by an audible indicator could change with changes in the operation status of a defibrillator. According to one embodiment, the audible indicator only produces a signal upon a change in the operation status of a defibrillator. In one case, the audible indicator would only produce a signal if the defibrillator becomes non-functional.

One specific embodiment includes two buttons. An inquiry is initiated upon pressing both buttons simultaneously for a period of time. Another specific embodiment transmits a status inquiry to the wireless communication port, thus initiating a status report.

Regardless of what type(s) of indicator is included in a system according to the present invention, the indicator may automatically produce indications of defibrillator status and/or produce the indications in response to user inquiry. If the device produces indications of defibrillator status in response to user inquiry, the device may include one or more user-activated triggers that can initiate a query of the functional status of a defibrillator. The trigger can include one or more buttons or other structures that a user employs to initiate a status query. Existing buttons on a defibrillator could serve the purpose of allowing a user to initiate a status inquiry.

Regardless of what buttons or other elements are employed for a user to initiate a status inquiry, a particular combination, sequence, and/or duration of activation of the buttons or other elements could initiate the inquiry. This could be particularly useful where existing buttons are utilized, thereby making a status inquiry possible without requiring additional structure. After initiation of the query, the indicator described above could indicate the results of the query.

However, reporting the results of the query can vary depending upon the embodiment. One embodiment a green LED can indicate functional status of a defibrillator and a red LED non-functional status. According to another embodiment, the results of the query could be displayed on a display. Alternative or additionally, one or more beeps, tones, or words could be produced to indicate functional or operational status of a defibrillator.

A defibrillator system according to the present invention may be designed to permit the user-initiated inquiry to be carried out whether or not the defibrillator is turned on. This may also be the case with embodiments that automatically report status of a defibrillator. Permitting determination of the status without requiring a defibrillator to be turned on represents an advantage over currently utilized systems, which typically require a defibrillator to be turned on before an inquiry can be initiated.

To permit monitoring of a defibrillator over time, a system according to the present invention can include a memory device for recording the status of a defibrillator. Whether the status is determined automatically or in response to user-initiated inquiries, a memory device can record the status. Any memory device may be used. Along these lines, the status may be recorded on a tape, disk, or other medium or stored on a memory structure, such as commonly available solid state memory devices. Any other memory device may also be utilized to record the status of a defibrillator.

One or more processors may be included in a defibrillator system according to the present invention for controlling the monitoring of the defibrillator, whether or not user-initiated, determination of defibrillator status, and/or the generation of the indication of the defibrillator status. A microcontroller may control timing of the indicator(s) as it/they indicate defibrillator status.

While the present invention has been discussed relative to a defibrillator, it may be utilized with a variety of electrotherapy devices. Electrotherapy devices include defibrillators, cardioverters and training devices that simulate the operation of an electrotherapy device. Defibrillators include automatic or semi-automatic external defibrillators (AEDs), including those defibrillators that deliver monophasic, biphasic or multiphasic waveforms externally to a patient.

Figure 3:
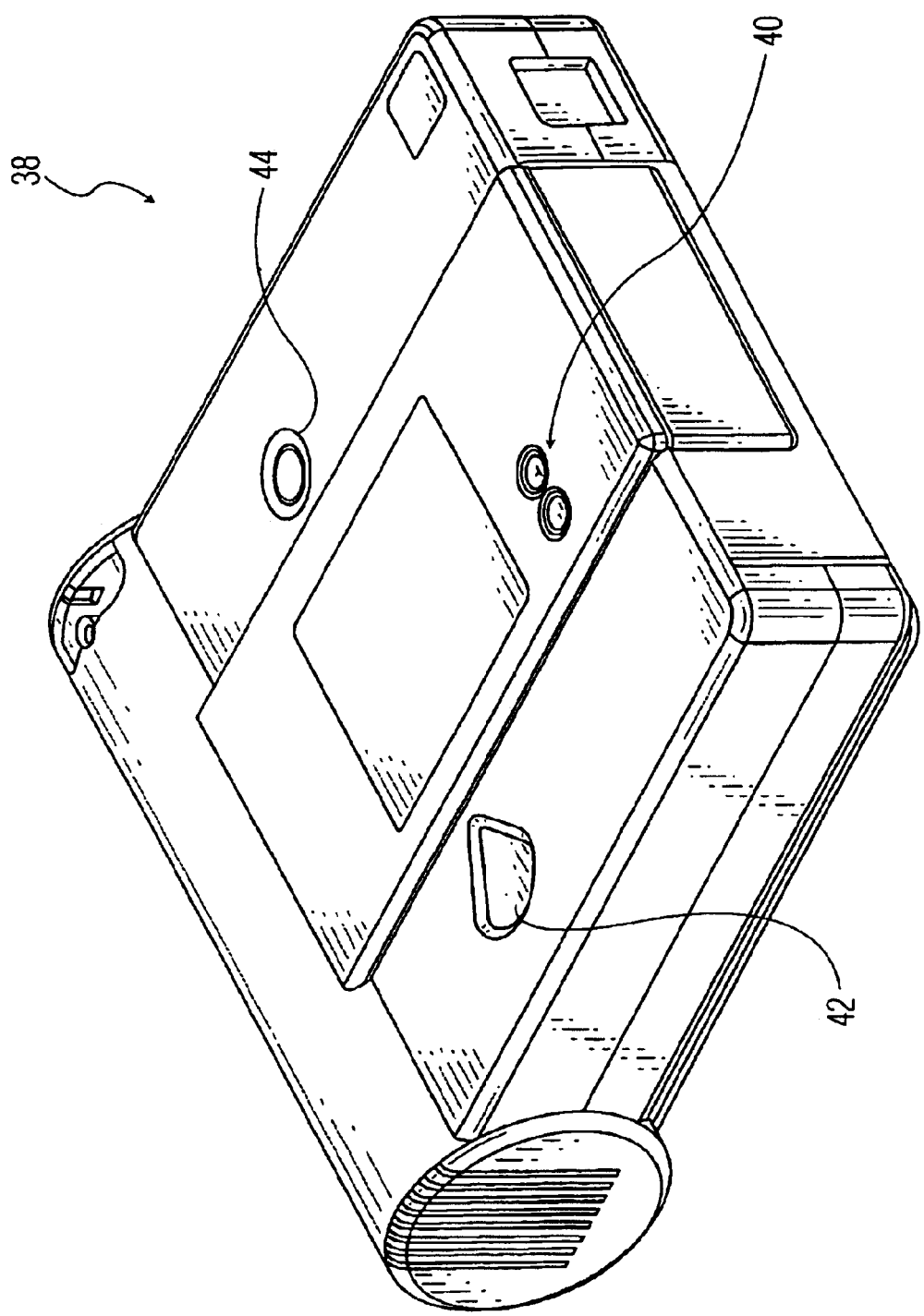
FIG. 3 represents an embodiment of a defibrillator according to the present invention.

FIG. 3 illustrates an embodiment of a defibrillator according to the present invention. Defibrillator 38 includes a visual indicator 40 and an audible indicator 42. The defibrillator also includes a trigger 44.

It is important to keep in mind that the present invention is flexible. The indication could be audible and/or visual. Also, the indication could be periodically produced and/or on demand or as triggered by a user. The triggering and/or the indication could be produced remote to the defibrillator.

The foregoing description of the invention illustrates and describes the present invention. Additionally, the disclosure shows and describes only the preferred embodiments of the invention, but as aforementioned, it is to be understood that the invention is capable of use in various other combinations, modifications, and environments and is capable of changes or modifications within the scope of the inventive concept as expressed herein, commensurate with the above teachings, and/or the skill or knowledge of the relevant art. The embodiments described hereinabove are further intended to explain best modes known of practicing the invention and to enable others skilled in the art to utilize the invention in such, or other, embodiments and with the various modifications required by the particular applications or uses of the invention. Accordingly, the description is not intended to limit the invention to the form disclosed herein. Also, it is intended that the appended claims be construed to include alternative embodiments.

What is claimed:

1. A defibrillator system, comprising:

a defibrillator, and at least one audible indicator connected to the defibrillator for generating an audible indication of a functional status of the defibrillator in response to a real-time user-triggered inquiry, wherein the functional status comprises a power level of a power source for the defibrillator.

2. A defibrillator system, comprising;

a defibrillator; and at least one indicator comprising at least one of at least one visual indicator and at least one audible indicator connected to the defibrillator for periodically generating at least one of an audible and a visual indication of a functional status of the defibrillator;

wherein the at least one indicator comprises a light source, and further wherein the at least one light source periodically blinks to indicate the functional status of the defibrillator, and still further wherein at least one of a frequency of the blinking and a color of the at least one light source varies with the functional status of the defibrillator.

3. A defibrillator system, comprising:

a defibrillator, and at least one audible indicator connected to the defibrillator for generating an audible indication of a functional status of the defibrillator in response to a real-time user-triggered inquiry, wherein at least one of a frequency of the generation, a pitch, and a volume of the audible signal varies with the functional status of the defibrillator.

4. A defibrillator system, comprising:

a defibrillator, and at least one audible indicator connected to the defibrillator for generating an audible indication of a functional status of the defibrillator in response to a real-time user-triggered inquiry, wherein the at least one indicator comprises an audible indicator that generates an audible signal to indicate a non-optimal status of the defibrillator.

5. The defibrillator system according to claim 4, wherein the audible indicator generates words to indicate a non-optimal status.

6. A defibrillator system, comprising:

a defibrillator, at least one audible indicator connected to the defibrillator for generating an audible indication of a functional status of the defibrillator in response to a real-time user-triggered inquiry, at least one user triggered indicator for indicating a functional status of the defibrillator, the user-triggered indicator comprising at least one user activated trigger for initiating a query of the functional status of the defibrillator, and a memory structure for recording results of the query of the functional status of the defibrillator.

7. A defibrillator system, comprising:

a defibrillator, at least one audible indicator connected to the defibrillator for generating an audible indication of a functional status of the defibrillator in response to a real-time user-triggered inquiry, at least one user triggered indicator for indicating a functional status of the defibrillator, the user-triggered indicator comprising at least one user activated trigger for initiating a query of the functional status of the defibrillator, wherein different colors of the indicator indicate the functional status of the defibrillator.

8. A defibrillator system, comprising:

a defibrillator, at least one audible indicator connected to the defibrillator for generating an audible indication of a functional status of the defibrillator in response to a real-time user-triggered inquiry, and a memory structure for recording functional status of the defibrillator.

* * * * *